United States Patent
Weber et al.

(10) Patent No.: US 9,651,637 B2
(45) Date of Patent: May 16, 2017

(54) METHOD FOR THE DETERMINATION OF A SPATIAL ASSIGNMENT OR SPATIAL DISTRIBUTION OF MAGNETIC PARTICLES

(71) Applicant: Bruker BioSpin MRI GmbH, Ettlingen (DE)

(72) Inventors: Alexander Weber, Karlsruhe (DE); Ulrich Heinen, Ettlingen (DE)

(73) Assignee: Bruker BioSpin MRI GmbH, Ettlingen (DE)

( * ) Notice: Subject to any disclaimer, the term of this patent is extended or adjusted under 35 U.S.C. 154(b) by 0 days.

(21) Appl. No.: 15/290,482

(22) Filed: Oct. 11, 2016

(65) Prior Publication Data

US 2017/0108560 A1 Apr. 20, 2017

(30) Foreign Application Priority Data

Oct. 15, 2015 (DE) .......... 10 2015 220 092

(51) Int. Cl.
*G01R 33/12* (2006.01)
*G01R 33/00* (2006.01)
(Continued)

(52) U.S. Cl.
CPC ..... *G01R 33/1276* (2013.01); *G01R 33/0029* (2013.01); *G01R 33/5601* (2013.01); *G06T 7/602* (2013.01); *G06T 11/005* (2013.01)

(58) Field of Classification Search
CPC ............ G01R 33/0029; G01R 33/1276; G01R 33/5601; G06T 11/005
See application file for complete search history.

(56) References Cited

U.S. PATENT DOCUMENTS 3,824,451 A * 7/1974 Freeman ............... G01R 33/46
324/312
7,898,252 B2 * 3/2011 Crozier .............. G01R 33/3415
324/307
(Continued)

OTHER PUBLICATIONS

Rahmer, J. et al., "Analysis of a 3-D system function measured for magnetic particle imaging", IEEE Transactions on Medical Imaging, 2012, vol. 31, No. 6, 1289-1299.
(Continued)

*Primary Examiner* — Dixomara Vargas
(74) *Attorney, Agent, or Firm* — Edell, Shapiro & Finnan, LLC (57) ABSTRACT

A method related to Magnetic Particle Imaging (MPI) includes a signal processing step in which MPI time signals are acquired and successive acquisition cycles are completed within one scanning period. From the scanning period, an image acquisition period is selected for which a composite time signal is generated by concatenating measured values acquired in immediate succession. A corrected time signal is determined from the composite time signal by windowing, performing a Fourier transform, and reducing a number of frequency values by eliminating intermediate frequencies of the Fourier transform of the windowed, composite time signal. In a reconstruction step, a spatial assignment and/or distribution of the magnetic particles is computed, and in an outputting step, the results of the reconstruction and/or one or more parameters derived therefrom are stored and/or displayed.

15 Claims, 6 Drawing Sheets

(51) Int. Cl.
  *G01R 33/56* (2006.01)
  *G06T 11/00* (2006.01)
  *G06T 7/60* (2017.01)

(56) References Cited

U.S. PATENT DOCUMENTS

| | | | | |
|---|---|---|---|---|
| 8,019,400 B2 * | 9/2011 | Diab | ................. | A61B 5/14546 |
| | | | | 600/323 |
| 8,364,226 B2 * | 1/2013 | Diab | ................. | A61B 5/14546 |
| | | | | 600/324 |
| 8,847,592 B2 * | 9/2014 | Goodwill | ................. | A61B 5/05 |
| | | | | 324/301 |
| 9,111,334 B2 * | 8/2015 | McCollough | ......... | G06T 11/005 |
| 9,140,769 B2 * | 9/2015 | van Zijl | ............. | G01R 33/5601 |
| 9,274,084 B2 * | 3/2016 | Goodwill et al. | ..... | G01R 33/10 |

OTHER PUBLICATIONS

Harris, F., "On the use of windows for harmonic analysis with the discrete fourier transform", Proceedings of the IEEE, vol. 66, No. 1, 1978, 51-83.

Gleich, B. et al., "Tomographic imaging using the nonlinear response of magnetic particles", Nature, vol. 435, 2005, 1214-1217.

Office Action in corresponding German Application No. 1020152200922, dated May 31, 2016, along with an English translation.

* cited by examiner

METHOD FOR THE DETERMINATION OF A SPATIAL ASSIGNMENT OR SPATIAL DISTRIBUTION OF MAGNETIC PARTICLES

CROSS REFERENCE TO RELATED APPLICATIONS

This application claims foreign priority under 35 U.S.C. §119(a)-(d) to German Application No. 10 2015 220 092.2 filed on Oct. 15, 2015, the entire contents of which are hereby incorporated by reference.

FIELD OF THE INVENTION

The invention relates to a method for the determination of the spatial distribution of magnetic particles in a specified analysis volume by means of an MPI (Magnetic Particle Imaging) measuring device.

BACKGROUND

Magnetic Particle Imaging (abbreviated to "MPI") is an imaging method which allows the spatial distribution of superparamagnetic nanoparticles (termed magnetic particles here) to be determined, as discussed in [01], for example. This is done by subjecting the magnetic particles in an analysis volume to different static and dynamic magnetic fields and detecting the changes in the magnetization of the magnetic particles using a receiving device. The receiving device is usually equipped with receiving coils for primary signal detection and contains further electronic and/or software components for signal digitization and for analog and digital conditioning and processing of the measurement signals recorded. With MPI, the spatial encoding is undertaken by applying a magnetic gradient field within the analysis volume, which has a field-free region. During an acquisition cycle, the field-free region is shifted along a predefined trajectory (specified course of each point of the field-free region) within the analysis volume with a scanning field (usually a superposition of the gradient field, a dynamic magnetic field (drive field) and/or homogeneous focusing fields). Driving the field-free region across the magnetic particles, and the associated change in magnetization, generates an MPI time signal which is detected by receiving coils. Image data representing the spatial distribution of the magnetic particles can be reconstructed from the MPI time signal.

Conventional MPI reconstruction methods use a discrete Fourier transform to transfer the MPI signal data (MPI time signal) which were recorded in the time domain into the spectral domain block by block. The discrete MPI spectra thus obtained are, however, susceptible to parasitic signals which have a broad spectral distribution due to the so-called leakage effect of the discrete Fourier transform and thus mask the intensity of real signals (useful signals). The MPI time signal recorded is therefore usually a superposition of a useful signal (signal which results from the magnetic particle distribution in the analysis volume) and one or more parasitic signals, e.g. parasitic interferences caused by the object under analysis, from signal transmission, quantization noise, and the like.

With many of the MPI data acquisition and MPI reconstruction techniques known to date, these parasitic signals, including the resulting image interferences, are accepted. A reconstruction is then possible only for comparatively strong useful signals, however. Broadband parasitic interferences may possibly lead to so-called flicker artifacts in the images obtained.

Averaging of several MPI time signals acquired in succession in order to thus reduce the proportion of parasitic signals in the MPI time signal is known from [02]. This leads immediately to a loss of time resolution, however. The number of averagings necessary for a defined damping of those parasitic signals which affect the spectrum via the leakage effect depends on the precise frequency position of the parasitic signal and can possibly be quite large.

Moreover, it is known that parasitic signals can be reduced by using suitable analog or digital filters (high pass, low pass, band stop) [03]. The precise position of the parasitic frequency must, however, be known in order to use filters in a way adapted to this purpose. This is not the case in general. Furthermore, these filters always affect relatively large frequency ranges, and therefore not only the parasitic frequency, but potentially also the useful signal is removed.

The application of window functions is known as an effective way of reducing the leakage effect [04]. A simple windowing leads to a broadening of the frequency spectrum of the individual frequencies (peak broadening), however. This applies to the MPI useful signal too, and thus leads to a mixing of signal components which are actually independent. This means that neither the amplitude accuracy nor the frequency selectivity is guaranteed, which leads to reconstruction artifacts, such that windowing cannot be used without compensation measures. Moreover, there are many different types of window functions which affect the amplitude accuracy, the peak broadening and the reduction of the leakage effect to varying degrees. The selection therefore becomes a difficult compromise.

A further option to reduce parasitic signals is to change the spectral distribution of the parasitic signal by changing the scanning period (period in which the measured values are acquired). With MPI, the minimum scanning period on which a single image is based is predetermined by the duration of an acquisition cycle of the field-free region. This means that, for MPI, an increase in the scanning period can only be achieved by recording of several acquisition cycles. If, however, the discrete Fourier transform is executed over the signal data of several successive cycles, this corresponds to an averaging with the same disadvantage of the loss of temporal resolution discussed above.

Moreover, reference signals which were recorded in a measurement shortly before or after the actual MPI measurement under the same measurement conditions, but without the object under analysis, can be subtracted from the MPI time signals. Apart from the fact that this method leads to a worsening of the signal-to-noise ratio, it is also not suitable to compensate for parasitic interferences which vary in frequency and/or phase from one acquisition cycle to the next, as is the case with the leakage effect.

SUMMARY

The present invention provides an MPI method whereby broadband parasitic interferences can be effectively suppressed without having to accept the above-mentioned disadvantages.

According to the inventive method, m MPI time signals with a total of m·N measured values $A_q$, where q=0, . . . , m·N−1, are acquired in an acquisition step by a receiving device of the MPI measuring device, and m successive acquisition cycles are completed within one scanning period, and in each of these acquisition cycles an MPI time signal of duration $T_0$ with N time-assigned measured values is acquired by executing the same specified measurement sequence, where m≥1 and N≥1. According to the invention, in a signal processing step:

a) one image acquisition period is selected from the scanning period, and for this image acquisition period a composite time signal with signal values $z_j$, where j=0, ..., n·N−1, is generated by concatenating n·N measured values acquired in immediate succession, where n≤m, and the measured value $A_r$, where 0≤r≤(m−n)·N−1, acquired at a desired starting time of the image acquisition period, is assigned to the start signal value $z_0$ so that $z_0 = A_r$, and an image acquisition period of duration n·$T_0$, is covered;

b) a corrected time signal $\tilde{z}$ is determined from the composite time signal z, and for this the determination of the corrected time signal $\tilde{z}$ comprises a windowing, a Fourier transform and a reduction of the frequency values by eliminating intermediate frequencies of the Fourier transform of the windowed, composite time signal.

In a reconstruction step, a spatial assignment and/or spatial distribution of the magnetic particles is computed from the reduced frequency spectrum generated in the signal processing step or from a corrected time signal computed by inverse Fourier transform of the reduced frequency spectrum. The results of the reconstruction and/or one or more parameters derived therefrom are ultimately stored and/or visualized in an outputting step.

The inventive method uses a combination of increasing the duration of the image acquisition period (n·$T_0$ instead of $T_0$) and a windowing adjusted to it (multiplication of the resulting composite time signal with the window function).

In the acquisition step, m acquisition cycles of length $T_0$ (cycle duration) are therefore completed initially within the scanning period, with the same measurement sequence being passed through in each cycle, while a field-free region is moved through the analysis volume by applying a magnetic scanning field. In this way, magnetic particles in the measurement volume are excited and an MPI time signal thus created is recorded by a receiving device of the MPI measuring device. The acquisition cycles or the executing of the measurement sequence are controlled by the MPI measurement device, and the individual acquisition cycles proceed in immediate succession without any gaps. The MPI signal generation process ensures that all frequency components occurring in the useful signal (useful signal components) are exact integer multiples of the cycle frequency $1/T_0$ (reciprocal of the cycle duration) for a static particle distribution in the image volume.

One image acquisition period of length n·$T_0$ is selected from the scanning period, such that the measured values intended for the further signal processing (windowing, discrete Fourier transform (DFT)) lie within this image acquisition period and the reduced frequency spectrum is ultimately generated from it.

If a DFT is carried out over an acquisition cycle of duration $T_0$ as part of the reconstruction step, the frequency resolution of the spectrum obtained is just about $1/T_0=f_0$ and all MPI useful signal components are imaged precisely on one single spectral position. In contrast, parasitic signals which are not stable in frequency, or whose frequencies are not integer multiples of $f_0$, are distributed in a broad band across the spectrum as a result of the leakage effect. The extension of the image acquisition period according to the invention, and thus the extension of the time interval of the discrete Fourier transform, to n acquisition cycles (image acquisition periods) means the spectral frequency resolution increases to $f_0/n$, with only each nth component having an n-fold averaged MPI useful signal, while parasitic signals occur distributed across all frequency components.

For the purpose of performing the windowing of step b, it is preferable for the signal values $z_j$ of the composite time signal z to be multiplied with interpolation points $w_j=w(t_j)$ of a window function w(t) which are appropriately assigned in terms of time, with the window function w(t) as a function of time being chosen so that the following formula applies at by approximation:

$$\hat{w}_k \equiv \sum_{j=0}^{nN-1} w_j e^{-i\frac{2\pi}{N}kj} = 0 \text{ where } k = l \cdot n \text{ for all } l = 1, \ldots, N-1,$$

whereby a resulting, composite time signal z' with resulting signal values $\acute{z}=z_j \cdot w_j$, where j=, ..., n·N−1, is generated. The resulting, composite time signal z' is obtained by windowing the composite time signal z. The window function is chosen so that the Fourier transform of the window function has zeros for all multiples of the cycle frequency. The maximum frequency selectivity is achieved in this case, which here means that frequencies with a frequency separation $f_0$ do not affect each other. However, it is in principle also sufficient if the Fourier transform of the window function has a damping for all multiples of the cycle frequency which is greater than the level difference between the largest parasitic signal and the signal noise. The window function is preferably normalized in accordance with $$\frac{1}{nN}\sum_{j=0}^{nN-1} w_j = 1,$$

this achieving amplitude accuracy for all frequencies which are integer multiples of $f_0$, i.e. amplitude accuracy for all MPI useful signals.

In one version of the inventive method, the Fourier transform and the reduction of the frequency values are executed in step b, whereby i. an extended frequency spectrum with N·n frequency values $F_0, F_1, \ldots F_{N*n-1}$ is firstly computed from the resulting composite time signal z' by a discrete Fourier transform, and ii. a reduced frequency spectrum with N frequency values $f_k$ is then generated from the extended frequency spectrum, where: $f_k = F_{k*n}$ for k=0, ..., N−1.

According to the invention, a reduced frequency spectrum is generated by discarding those values of the extended frequency spectrum for intermediate frequencies $$\frac{nk+1}{n}f_0, \ldots, \frac{nk+(n-1)}{n}f_0 \text{ where } k \in \mathbb{N},$$

which have been newly added by increasing the time interval over which the discrete Fourier transform is executed to n acquisition cycles. Due to the specific properties of the MPI signal generation these intermediate frequencies can fundamentally never carry a useful signal and therefore discarding the values for these intermediate frequencies according to the invention does not lead to losses regarding the useful signal.

The corrected time signal can be computed from the reduced frequency spectrum using an inverse Fourier transform.

The windowing of the composite time signal and/or its Fourier transform and/or the discarding of the intermediate frequencies (selecting the frequencies of the reduced frequency spectrum $f_k = F_{k*n}$) and/or the execution of an inverse Fourier transform, as intended in the signal processing, do not necessarily have to be separate steps of the method, but can also be carried out directly in a joint procedural step by explicitly computing only the frequencies used afterwards $f_k = F_{l*n}$) or the corrected time signal using a matrix operation which implicitly contains several of these operations (the windowing of the composite time signal and/or its Fourier transform and/or the discarding of the intermediate frequencies and/or the inverse Fourier transform). The Fourier transform, including the discarding of individual frequencies, can be realized by a matrix multiplication with a reduced Fourier matrix (=Fourier matrix×Elimination matrix), for example.

A special version of the inventive method therefore provides for the Fourier transform and the reduction of the frequency values to be carried out in step b by applying a matrix operator C' to the resulting, composite time signal z', with $\tilde{z} = F'^{-1} R F z' = C'z'$, where F is a Fourier matrix of dimension n·N×n·N, R is a matrix of dimension n·N×N with the coefficients $r_{ij} = \delta_{(n \cdot i),j}$, which eliminates the intermediate frequencies, and $F'^{-1}$ is an inverse Fourier matrix of dimension N×N.

It is even possible for all the processing steps from step b for correcting the time signal to be combined in a single matrix operator C.

In this version, the windowing, the Fourier transform and the reduction of the frequency values is thus carried out in step b by applying a matrix operator C to the composite time signal z, with $\tilde{z} = F'^{-1} R F W z = C z$, where W is a diagonal matrix of dimension n·N×n·N whose diagonal elements are the interpolation points $w_j$ of a discretized window function w(t) which is chosen as a function of time in such a way that the following applies at least by approximation:

$$\hat{w}_k \equiv \sum_{j=0}^{nN-1} w_j e^{-i\frac{2\pi}{N}kj} = 0 \text{ where } k = l \cdot n \text{ for all } l = 1, \ldots, N-1,$$

F is a Fourier matrix of dimension n·N×n·N, R a matrix of dimension n·N×N with the coefficients $r_{ij} = \delta_{(n \cdot i),j}$ which eliminates the intermediate frequencies, and $F'^{-1}$ an inverse Fourier matrix of dimension N×N.

It is, moreover, also possible to execute other combinations of the operations to be carried out in step b with the aid of one or more matrix operations.

The four matrix operators can therefore be combined in parts or as a whole into an n·N×N matrix which directly computes the corrected and reduced time data $\tilde{z}_k$ where k= 0, . . . , N−1 from the signal values $z_j$ of the composite time signal z.

Since an efficient algorithm for the computation of the Fourier transform exists (FFT), it can possibly be more efficient, given the data quantities relevant in MPI, to compute the complete spectrum and subsequently eliminate frequencies, instead of computing the desired frequencies via such a matrix method in a single step.

The spatial distribution computed in the reconstruction step can describe the distribution of a specific type of magnetic particle, and also of several different types of magnetic particles.

The signal processing according to the invention can compute a corrected time signal and/or a frequency spectrum with reduced parasitic interference for each image acquisition period, and thus generate a spatial distribution and/or spatial assignment of the magnetic particles with reduced parasitic effects and artifacts.

One version of the inventive method provides that the sideband suppression of the window function w(t) is larger than the parasitic signal/noise ratio of the composite time signal. The term parasitic signal/noise ratio is used to mean the maximum separation between parasitic level and noise level. The sideband suppression is typically given by the maximum of the first side lobe of the Fourier transformed window function (Peak Side Lobe Level, PSLL). If the sideband suppression exceeds at least the parasitic signal/noise ratio, the leakage effect does not make a significant contribution to the composite signal. The maximum sensible sideband suppression results from the dynamic range of the receiving system used. If the dynamic resolution is 100 dB, for example, it is no longer possible to recognize a difference between a sideband suppression of 100 dB or more, since the values cannot be measured in the first place.

Of the window functions possible according to this criterion, it is preferable to select the one which fulfills this conditions with smallest possible n∈ℕ.

In a special version of the inventive method, m=n is set. This means all MPI time signals are then evaluated in the signal processing step, and a spatial assignment and/or distribution of the magnetic particles is computed for the complete scanning period.

Alternatively, it is also possible to use only some of the MPI time signals acquired in the acquisition step within the scanning period for one signal processing step, i.e. n<m is selected. Within the scanning period, a shorter (continuous) image acquisition period is then chosen with an image acquisition starting time with start index r, for which the further signal processing steps are carried out.

In accordance with the specification of different desired image acquisition starting times, several image acquisition periods can be selected for one and the same scanning period by choosing permissible values for the time signal start index r. One special version of the inventive method therefore provides that the signal processing, reconstruction and outputting step is completed with different starting times for each of the different image acquisition periods of the same duration. Several image acquisition periods are therefore processed for each scanning period and, correspondingly, several spatial assignments and/or distributions of the magnetic particles are computed. The different image acquisition periods differ in the choice of the index r for the measurement point $A_r$, which in each case is assigned to the start signal value $z_0$ of the corresponding composite time signal. In this way, a spatial distribution of the magnetic particles within different predetermined time intervals is achieved. This allows a determination of the temporal development of the spatial distribution of magnetic particles to be undertaken, e.g. to visualize dynamic processes which exhibit significant changes with a rate of change of the order of the cycle frequency. The image acquisition periods can temporally overlap here. The temporal overlap is preferably an integer multiple of the duration $T_0$ of an acquisition cycle. The overlap can, however, also be chosen in such a way that any number of measurement points, in the extreme case also all but one data point of an acquisition cycle, are contained in the overlap. There can also be a provision for leaving time gaps between the different image acquisition periods, however. For shifts less than $T_0$, it is only necessary to correct a changed phase angle of the resulting spectra.

To investigate dynamic processes with rates of change that are less than the cycle frequency, the inventive method can be repeated for different (non-overlapping) scanning periods. For reasons of efficiency, however, the special case of scanning period and image acquisition period of equal length is preferred. The starting times of the successive scanning periods can be equidistant or can be set according to different criteria to suit the specific analysis. Successive scanning periods will usually be separated by scanning gaps to reduce the quantity of measurement data.

The two above-described versions of the method for the investigation of dynamic processes can also be combined so that MPI signals are therefore acquired in several scanning periods, and several image acquisition periods are selected and evaluated for each scanning period in order to link together the cases of the small and large rates of change and detect both image dynamics simultaneously.

The inventive method can also be used to effectively reduce broadband parasitic signals originating from monochromatic parasitic signals which do not lie on the DFT frequency grid.

Further advantages of the invention are apparent from the description and the illustrations. Likewise, the above-named features and those explained in more detail can each be used either individually or several together in any chosen combination according to the invention. The embodiments shown and described are not to be understood as a complete list but rather as examples for the description of the invention.

DETAILED DESCRIPTION

Figure 1A:
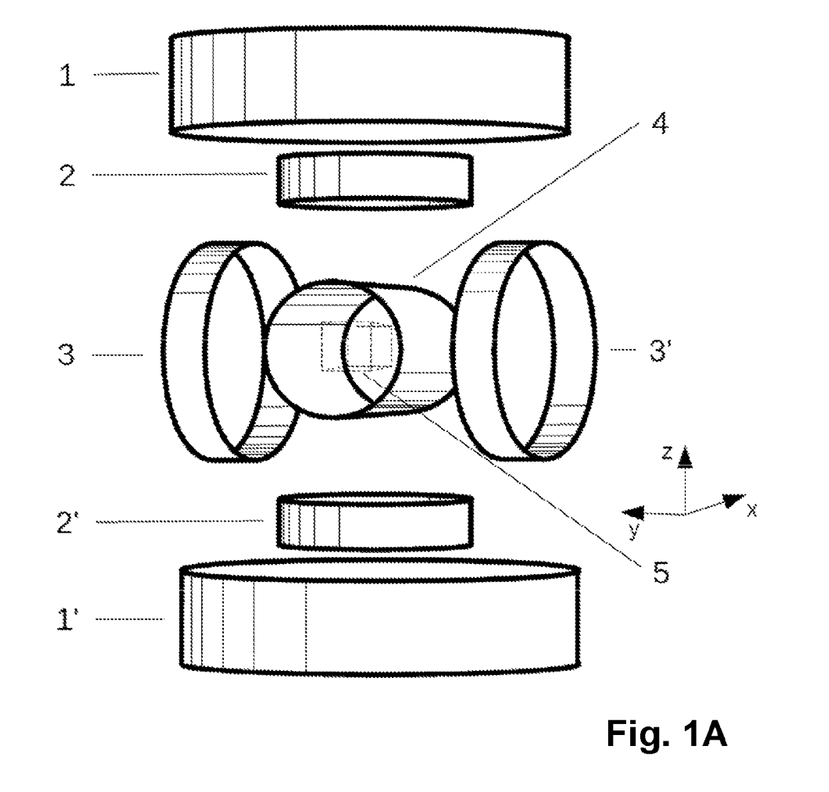
FIG. 1A shows a schematic representation of an MPI magnetic system suitable for carrying out the inventive method.
Figure 1B:
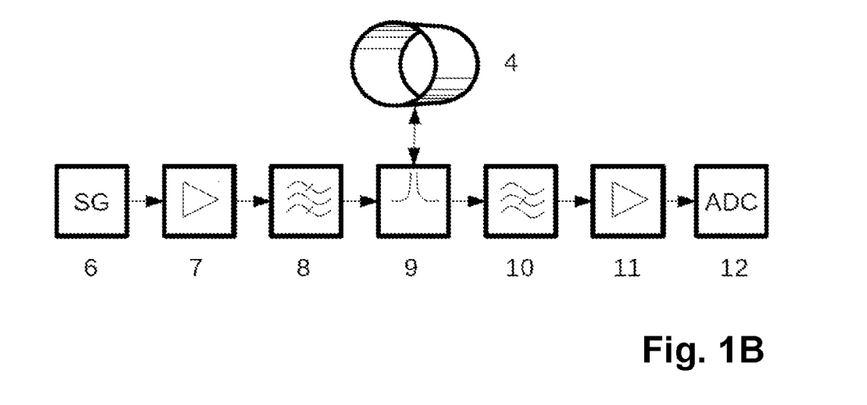
FIG. 1B shows schematically the structure of a single measurement channel of an MPI instrument suitable for carrying out the inventive method.

FIG. 1A shows an MPI magnetic system with gradient coils 1/1' and transmission and receiving coils 2/2', 3/3', 4 along three orthogonal spatial axes x, y, z, where the transmission and receiving coils 2/2', 3/3" take the form of Helmholtz coil pairs, and the transmission and receiving coils 4 take the form of solenoid coils. Reference numeral 5 refers to an analysis volume of the MPI magnetic system within which magnetic particles are arranged and whose spatial distribution is to be determined. In FIG. 1B, the associated transmission and receiving device for solenoid coil 4 is illustrated by way of example. Here, numeral 6 refers to a digital signal generator, numeral 7 a transmission amplifier, numeral 8 a bandpass filter to ensure a monochromatic excitation, numeral 9 a coupling and matching network, numeral 10 a bandstop filter complementary to the coupling and matching network 9, numeral 11 a receiving amplifier, and numeral 12 a receiver which contains further electronic and/or software components for signal digitization and analog and digital conditioning and processing of the measurement signals recorded.

Figure 2A:
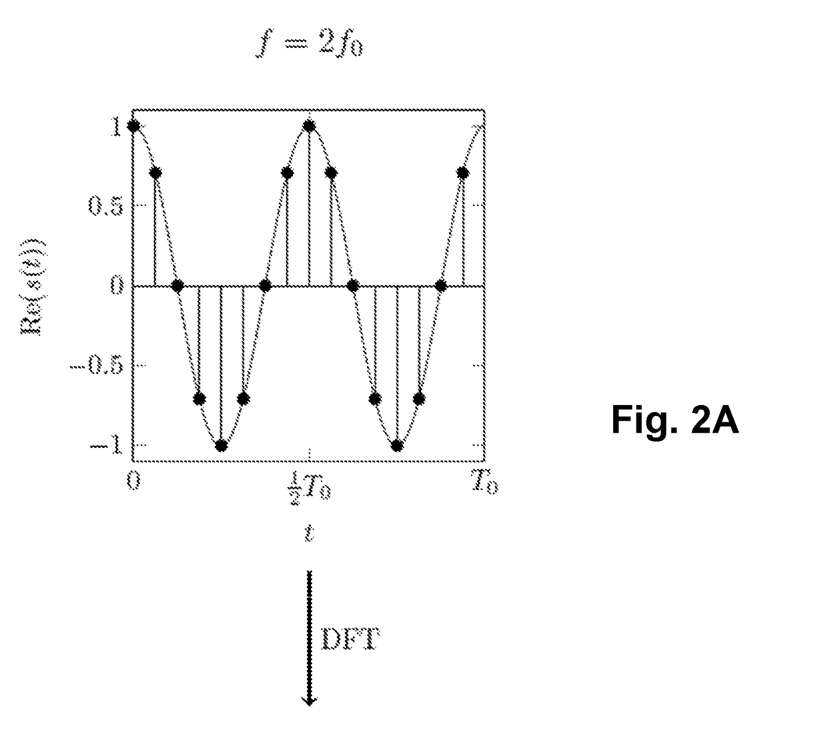
FIG. 2A shows an MPI time signal within a minimum scanning period with 8 measured values for a useful signal.

The inventive method is illustrated, with the aid of the complex exponential function $s(t)=e^{-i2\pi f T_0 t}$, as a model for a signal curve. Although an MPI time signal contains data with real values, this special case can be treated analogously to the illustrative example. FIGS. 2A, 3A show the temporal curve of the real part of s(t) for $f=2f_0$ (FIG. 2A) or for $f=2.25f_0$ (FIG. 3A), each for a scanning period of the cycle duration $T_0$. With MPI, $T_0$ corresponds to the length of the time interval to complete one acquisition cycle, i.e. the minimum scanning period. The situation according to FIG. 2A corresponds to a useful signal because s(t) has a period of $T_0$. The situation according to FIG. 3A, in contrast, corresponds to a parasitic signal because s(t) has a period different from $T_0$. With a real MPI time signal, useful and parasitic signals are superimposed. The frequency spectra F(k) in FIGS. 2B and 3B, obtained by discrete Fourier transform (DFT) from the useful or parasitic signal in accordance with FIGS. 2A and 3A, show that, in the case of the purely useful signal, a single frequency (k=2) is detected, while in the case of the parasitic signal, parasitic signal contributions are distributed across all frequencies.

In order to illustrate the different effects of the inventive method on a useful signal and a parasitic signal, the inventive method is applied, in the following, to the purely useful signal (FIGS. 4A-D) and the purely parasitic signal (FIGS. 5A-D) of the chosen example.

Firstly, the signal in question, i.e. the useful signal or the parasitic signal, is acquired for an extended scanning period A (time interval to complete the m acquisition cycles) of duration $3 \cdot T_0$ (m=3). This means that each time one additional repetition is acquired before and after the actual acquisition cycle. The data recording can be started at any chosen time. The scanning period A shown in FIGS. 4A and 5A therefore has three acquisition cycles, each containing 8 measured values (N=8). According to the invention, an image acquisition period B (totality of the time intervals of the n acquisition cycles which are processed in the signal processing step and from which an image is usually reconstructed) is selected from the scanning period A. In the present example, the image acquisition period B is chosen to be identical with the scanning period A (m=n=3), while the 24 measured values acquired within the image acquisition period B form a composite time signal z(t). Care must be taken here that the image acquisition period B contains acquisition cycles which follow in immediate succession.

The composite time signal z(t) is multiplied with a window function w(t) in the time domain. According to the invention, the window function w(t) is adapted to the parasitic signal/noise ratio of the measuring device, i.e. a window function is used whose sideband suppression is larger than the parasitic signal/noise ratio of the composite time signal z(t).

Figure 4A:
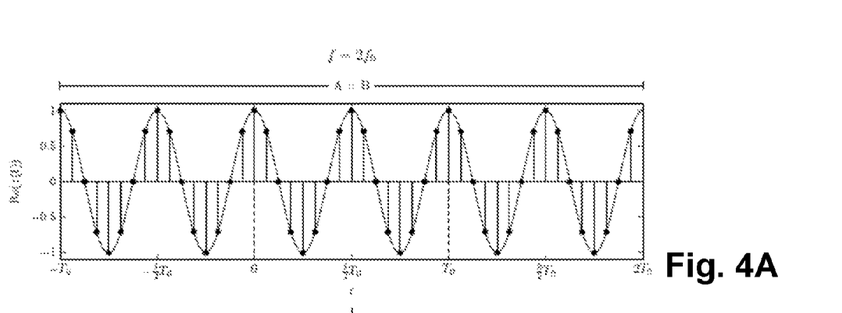
FIG. 4A shows a composite time signal within an extended scanning period with 24 measured values for a useful signal.
Figure 4B:
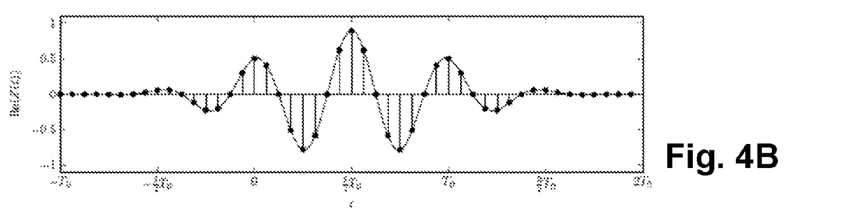
FIG. 4B shows a resulting composite time signal, with an image acquisition period of duration $3T_0$, obtained from the composite time signal of FIG. 4A.
Figure 4C:
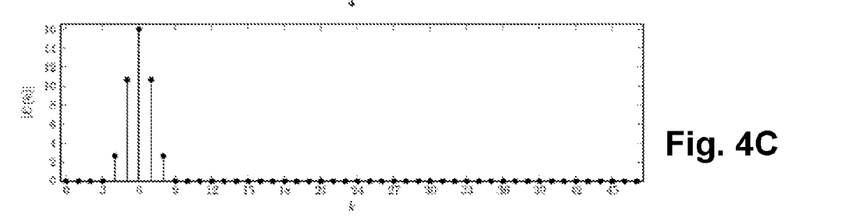
FIG. 4C shows an extended frequency spectrum obtained from the resulting composite time signal of FIG. 4B.
Figure 4D:
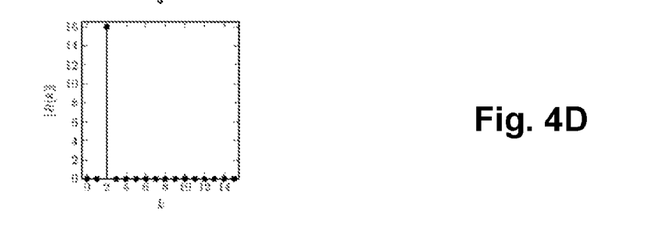
FIG. 4D shows a reduced frequency spectrum obtained from the extended frequency spectrum of FIG. 4C.
Figure 5A:
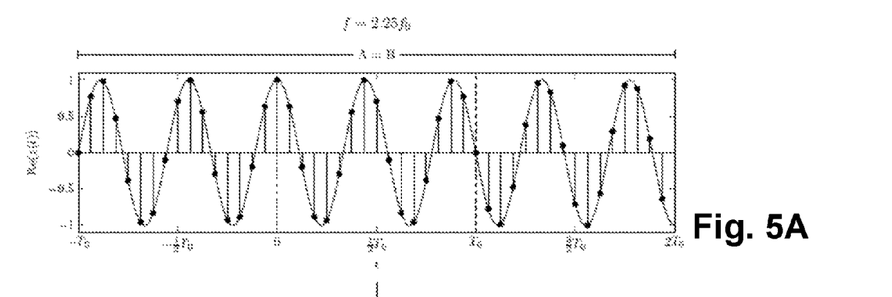
FIG. 5A shows a composite time signal within an extended scanning period with 24 measured values for a parasitic signal.
Figure 5B:
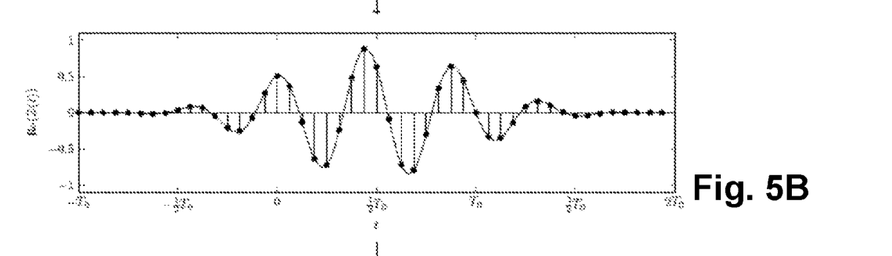
FIG. 5B shows a resulting composite time signal, with an image acquisition period of duration $3T_0$, obtained from the composite time signal of FIG. 5A.
Figure 5C:
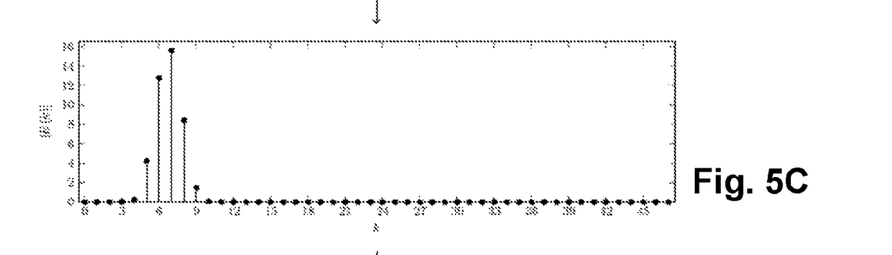
FIG. 5C shows an extended frequency spectrum obtained from the resulting composite time signal of FIG. 5B.
Figure 5D:
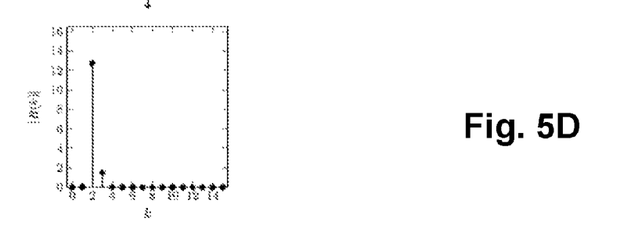
FIG. 5D shows a reduced frequency spectrum obtained from the extended frequency spectrum of FIG. 5C.

FIGS. 4B and 5B show composite time signals Z(t) resulting from the application of the windowing for the two cases of the purely useful and the parasitic signal.

Figure 2B:
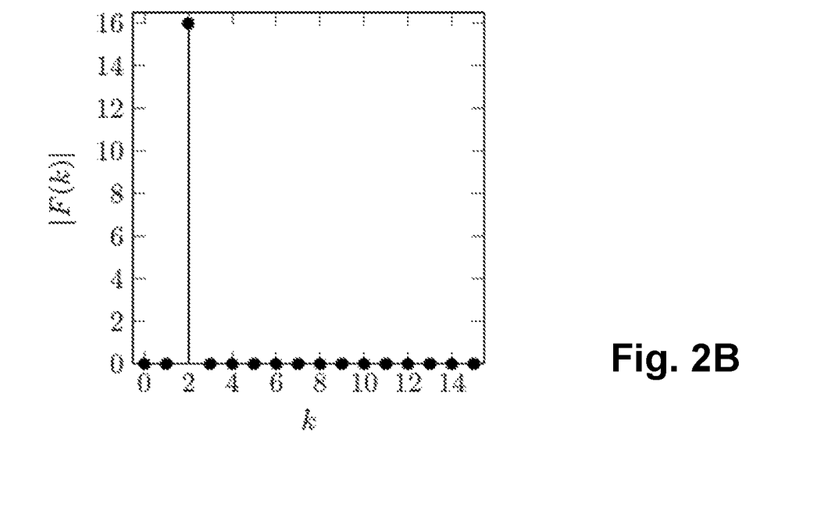
FIG. 2B shows a frequency spectrum obtained from the MPI time signal of FIG. 2A.
Figure 3A:
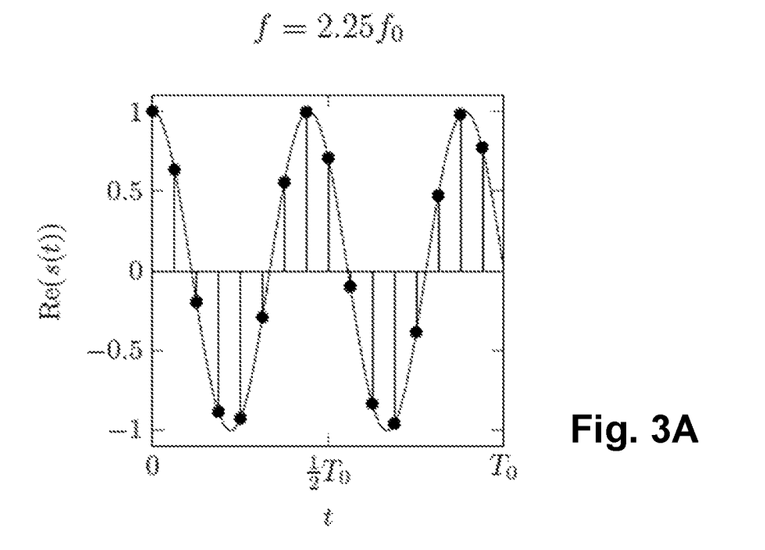
FIG. 3A shows an MPI time signal within a minimum scanning period with 8 measured values for a parasitic signal.
Figure 3B:
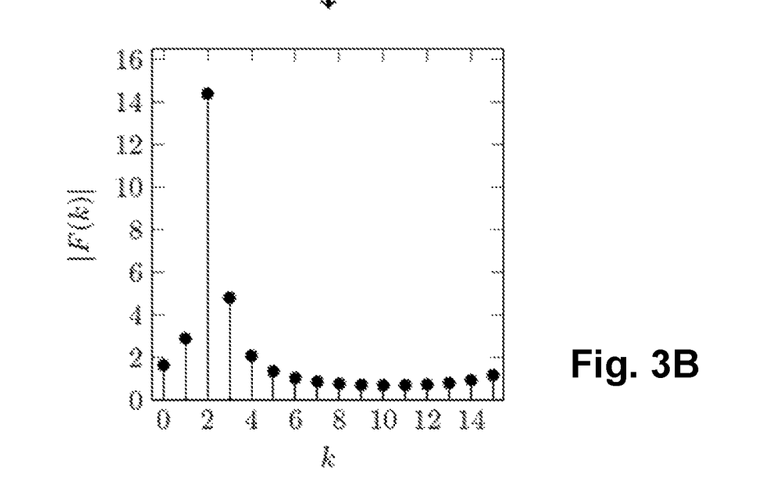
FIG. 3B shows a frequency spectrum obtained from the MPI time signal of FIG. 3A.

A discrete Fourier transform is carried out in accordance with the invention for the signal data of the resulting, composite time signal Z(t), and an extended frequency spectrum E(k) (FIGS. 4C, 5C) is obtained, where every third frequency of the extended frequency spectrum E(k) now corresponds to a frequency from the frequency spectrum F(k) of the individual acquisition cycle from FIGS. 2B, 3B.

The window function w(t) was chosen so that the Fourier transform of the window function w(t) has zeros for all multiples of the cycle frequency $1/T_0$. In this case, a $\cos^4$ window function was used [4], which in the present case of two additional repetitions to the actual acquisition cycle in the extended frequency spectrum E(k) does not exceed a bilateral peak broadening by two neighboring spectral positions. In this way, the largest possible suppression of the leakage effect is achieved (the greater the peak broadening, the better the suppression of the leakage effect) and at the same time a maximum broadening of the principle maximum by two spectral positions. The selected window function w(t) directly ensures amplitude accuracy for frequencies on the discrete grid of the discrete Fourier transform.

Since all useful signals for MPI measurements lie on the frequency grid of a single acquisition cycle, the complete useful signal is contained on the frequency grid of the individual acquisition cycle. All other frequencies can be assigned to a parasitic interference and thus discarded. By rejecting the intermediate frequencies according to the invention, a reduced frequency spectrum R(k) (FIGS. 4D and 5D) with discrete frequency values is obtained, corresponding to the frequency grid of the individual acquisition cycle from FIGS. 2A, 3A.

The results of the windowing, the discrete Fourier transform, and the discarding of the intermediate frequencies are shown in separate graphic representations in FIGS. 4B-D and 5B-D. When a direct method is used, where the windowing, the Fourier transform and the reduction of the frequency values is carried out using a matrix operation, the resulting (i.e. the windowed) composite time signal and/or the extended frequency spectrum is not generated, but the desired frequencies are computed directly.

A comparison of the reduced frequency spectra R(k) for the cases of the purely useful signal (FIG. 4D) and the parasitic signal (FIG. 5D), on the one hand, and the frequency spectra F(k) of the individual acquisition cycle for the useful signal (FIG. 2B) and the parasitic signal (FIG. 3B), on the other hand, shows that the useful signal is not impaired by the signal processing according to the invention, whereas the leakage effect of the parasitic signal is significantly reduced. It can thus be seen that the parasitic signal now only makes a significant contribution at two frequency positions, whereas without correction it is distributed across the whole spectrum shown. The correction means that the principal intensity is imaged to the frequency k=2 and a small residual to k=3. In contrast to this example, real experiments always have a noise background too. In this case, the sidebands can be successfully lowered below the experimental noise with a suitably selected filter function.

MPI time signals whose parasitic signals have been removed can be regained by inverse transformation of the filtered spectra (inverse discrete Fourier transform) into the time domain.

The windowing carried out by the inventive method means that signal contributions at the beginning and end of the image acquisition period (and thus of the DFT interval) enter the computation of the extended frequency spectrum E(k), and thus also the reduced frequency spectrum R(k), with only a low amplitude. The effective temporal resolution of a reduced frequency spectrum according to the invention is therefore worse than the duration $T_0$ of the acquisition cycle, but always better than the duration $nT_0$ of the image acquisition period B. When reconstructing an image series using a DFT interval increased to the duration $nT_0$ of the image acquisition period B, successive images from successive overlapping image acquisition periods of the original data stream can be reconstructed so that the increase of the DFT interval does not necessarily coincide with a reduction of the image rate.

The following steps enable frequency spectra with reduced parasitic interference to be computed without having to accept disadvantages in terms of amplitude accuracy and frequency selectivity: selection of a window function, according to the invention, which is adapted to the parasitic signal/noise ratio of the measurement system in respect of its sideband suppression; coordination of image acquisition period B and window function w(t) in regard to the first zero of the window function w(t) in the frequency domain; and the loss-free—due to the special MPI signal properties—discarding of the intermediate frequencies, which are added because of the increased image acquisition period B compared to the acquisition cycle.

Figure 6:
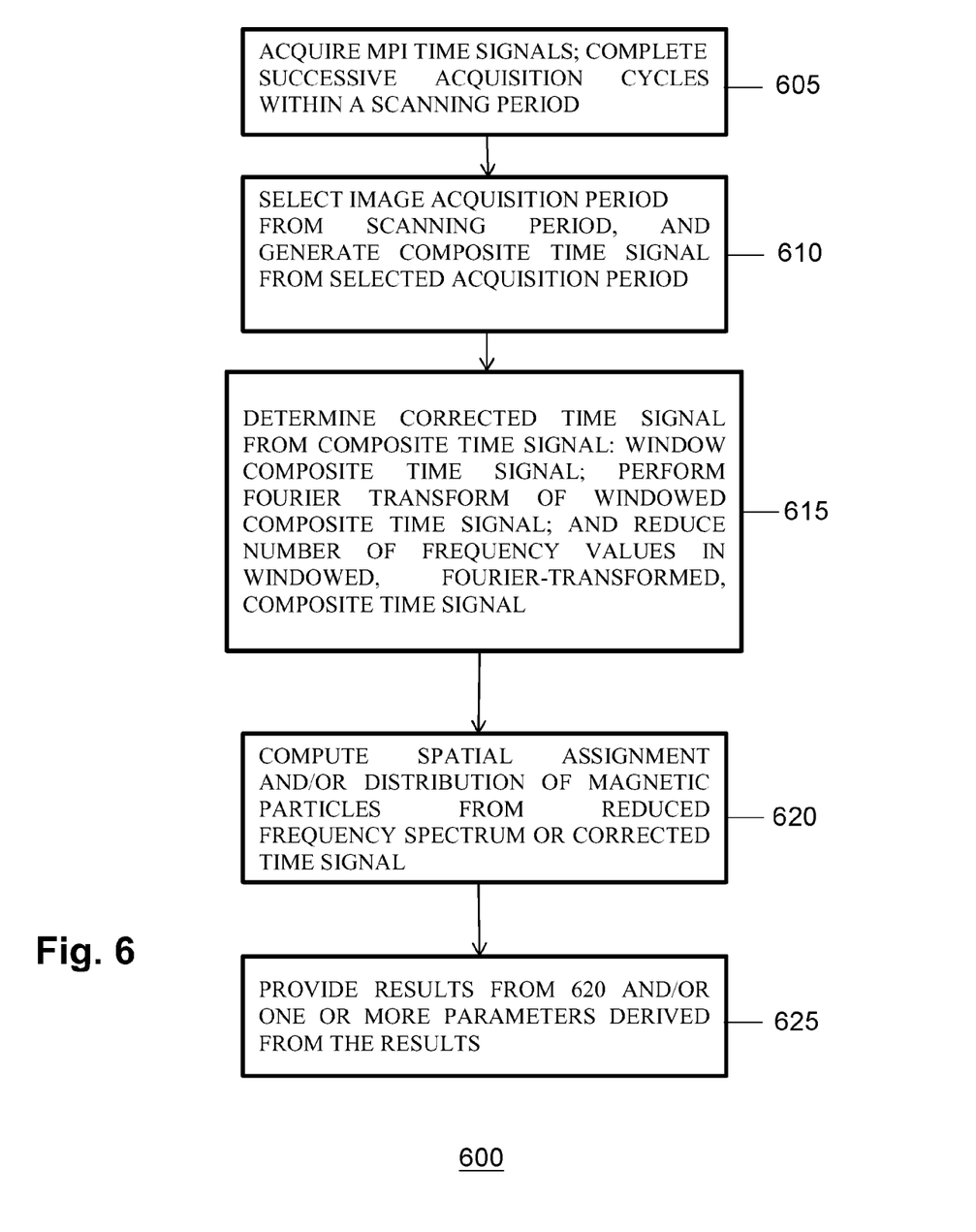
FIG. 6 shows a flowchart of an example method for determining a spatial assignment or spatial distribution of magnetic particles.

FIG. 6 is a high-level flowchart of an example method 600 for determining a spatial assignment or spatial distribution of magnetic particles that summarizes operations described in detail above. Method 600 may be performed by the measurement channel of the MPI instrument described above in connection with FIG. 1A.

At 605, in an acquisition step, MPI time signals are acquired, and successive acquisition cycles within a scanning period are completed.

At 610, in a first signal processing step, an image acquisition period is selected from the scanning period, and a composite time signal is generated from the selected acquisition period.

At 615, in a second signal processing step, a corrected time signal is determined from the composite time signal. To do this: the composite time signal is windowed; a Fourier transform of the windowed composite time signal is performed, which produces a number of frequency values; and the number of frequency values is reduced to produce a reduced frequency spectrum.

At 620, in a reconstruction step, a spatial assignment and/or distribution of magnetic particles is computed from either the reduced frequency spectrum or the corrected time signal.

At 625, in an outputting step, results from the reconstruction and/or at least one parameter derived from the reconstruction are provided, which may include storing and/or displaying the results.

LIST OF REFERENCES

[01] B. Gleich, and J. Weizenecker. "Tomographic imaging using the nonlinear response of magnetic particles." Nature 435.7046 (2005): 1214-1217.
[02] J. Rahmer et al. "Analysis of a 3D System Function Measured for Magnetic Particle Imaging" IEEE Transactions on medical imaging, 2012, Volume: 31, Issue: 6, pp. 1289-1299
[03] U. Tietze, C. Schenk and E. Gamm. Halbleiter-Schaltungstechnik. Springer-Verlag, 2002, 12th edition
[04] J. F. Harris, "On the use of windows for harmonic analysis with the discrete Fourier transform." Proceedings of the IEEE 66.1 (1978): 51-83.

LIST OF REFERENCE SIGNS

1/1 Gradient coils
2/2' Transmission and receiving coils
3/3 Transmission and receiving coils
4 Transmission and receiving coil
5 Analysis volume
6 Digital signal generator
7 Transmission amplifier
8 Bandpass filter
9 Coupling and matching network
10 Bandstop filter
11 Receiving amplifier
12 Receiver
A Scanning period
B Image acquisition period
F(k) Frequency spectrum of an individual acquisition cycle
E(k) Extended frequency spectrum of the resulting, composite time signal
R(k) Reduced frequency spectrum
x, y, z Orthogonal spatial axes
s(t) Time signal of an individual acquisition cycle
w(t) Window function
z(t) Composite time signal of the image acquisition period
Z(t) Composite time signal obtained after windowing

What is claimed is:

1. A method of determining a spatial assignment and/or spatial distribution of magnetic particles in a specified analysis volume performed by a Magnetic Particle Imaging (MPI) measuring device, comprising:
in an acquisition step performed with a receiving device of the MPI measuring device, acquiring m MPI time signals with a total of m·N measured values $A_q$, where $q=0, \ldots, m \cdot N-1$, completing m successive acquisition cycles within a scanning period, and in each of the acquisition cycles acquiring an MPI time signal of duration $T_0$ with N time-assigned measured values by repeatedly executing a specified measurement sequence, where m≥1 and N≥1;
in a signal processing step:
a) selecting one image acquisition period from the scanning period and, for the selected image acquisition period, generating a composite time signal z with signal values $z_j$, where $j=0, \ldots, n \cdot N-1$, by concatenating n·N measured values acquired in immediate succession, where n≤m, acquiring at a desired starting time of the image acquisition period a measured value $A_r$, with $0 \le r \le (m-n) \cdot N-1$, and assigning the measured value $A_r$ to a start signal value $z_0$ so that $z_0 = A_r$, and an image acquisition period of duration $n \cdot T_0$, is covered; and
b) determining a corrected time signal $\tilde{z}$ from the composite time signal z, wherein the determining the corrected time signal $\tilde{z}$ comprises windowing the composite time signal z to produce a windowed composite time signal, computing a Fourier transform of the windowed composite time signal to produce a windowed, Fourier-transformed, composite time signal having a number of frequency values, and reducing the number of frequency values by eliminating intermediate frequencies among the number of frequency values to produce a reduced frequency spectrum;
in a reconstruction step, computing the spatial assignment and/or the spatial distribution of the magnetic particles from either the reduced frequency spectrum or the corrected time signal $\tilde{z}$; and
in an outputting step, providing results of the reconstruction and/or at least one parameter derived from the reconstruction.

2. The method according to claim 1, wherein the windowing includes multiplying the signal values $z_j$ of the composite time signal z with interpolation points $w_j = w(t_j)$ of a window function w(t), wherein the interpolation points are correspondingly assigned in terms of time, and the window function w(t) as a function of time is selected so that the following applies at least by approximation:

$$\hat{w}_k \equiv \sum_{j=0}^{nN-1} w_j e^{-i\frac{2\pi}{N}kj} = 0 \text{ where } k = l \cdot n \text{ for all } l = 1, \ldots, N-1,$$

to produce a resulting, composite time signal z' with resulting signal values $Z_j = z_j \cdot w_j$, where $j=0, \ldots, n \cdot N-1$.

3. The method according to claim 2, wherein:
the computing of the Fourier transform includes computing a discrete Fourier transform from the resulting composite time signal z' to produce an extended frequency spectrum with N·n frequency values $F_0, F_1, \ldots, F_{N \cdot n-1}$; and
the reducing includes generating from the extended frequency spectrum the reduced frequency spectrum with N frequency values $f_k$, where: $f_k = F_{k \cdot n}$ for $k=0, \ldots, N-1$.

4. The method according to claim 3, wherein the corrected time signal $\tilde{z}$ is computed by performing an inverse Fourier transform of the reduced frequency spectrum.

5. The method according to claim 2, wherein the computing of the Fourier transform and the reducing collectively include applying a matrix operator C' to the resulting, composite time signal z', with $\tilde{z} = F'^{-1} R F z' = C' z'$, where
F is a Fourier matrix of dimension n·N×n·N,
R is a matrix of dimension n·N×N with the coefficients $r_{ij} = \delta_{(n \cdot i),j}$ which eliminates the intermediate frequencies, and
$F'^{-1}$ is an inverse Fourier matrix of dimension N×N.

6. The method according to claim 2, wherein the window function w(t) has a sideband suppression that is greater than a parasitic signal/noise ratio of the composite time signal z.

7. The method according to claim 2, wherein m=n.

8. The method according to claim 2, wherein n<m.

9. The method according to claim 1, further comprising repeating the signal processing step, the reconstruction step, and the outputting step for each of different image acquisition periods that have respective durations that are equal to each other but respective starting times that differ from each other.

10. The method according to claim 9, wherein the starting times of the different image acquisition periods differ by integer multiples of $T_0$.

11. The method according to claim 1, wherein the windowing, the performing of the Fourier transform, and the reducing collectively include applying a matrix operator C to the composite time signal z, with $\tilde{z}=F'^{-1}RFWz=Cz$, where W is a diagonal matrix of dimension $n \cdot N \times n \cdot N$, whose diagonal elements are interpolation points $w_j$ of a discretized window function $w(t)$, which is chosen as a function of time such that the following applies at least by approximation:

$$\hat{w}_k \equiv \sum_{j=0}^{nN-1} w_j e^{-i\frac{2\pi}{N}kj} = 0 \text{ where } k = l \cdot n \text{ for all } l = 1, \ldots, N-1,$$

F is a Fourier matrix of dimension $n \cdot N \times n \cdot N$,
R is a matrix of dimension $n \cdot N \times N$ with the coefficients $r_{ij}=\delta_{(n \cdot i),j}$ which eliminates the intermediate frequencies, and $F'^{-1}$ is an inverse Fourier matrix of dimension $N \times N$.

12. The method according to claim 1, wherein the windowing includes multiplying the composite time signal z by a window function $w(t)$ having a sideband suppression that is greater than a parasitic signal/noise ratio of the composite time signal z.

13. The method according to claim 1, wherein m=n.

14. The method according to claim 1, wherein n<m.

15. The method according to claim 1, wherein the providing comprises storing and/or displaying the results of the reconstruction.

* * * * *